(12) United States Patent
Senn-Bilfinger et al.

(10) Patent No.: US 6,197,783 B1
(45) Date of Patent: Mar. 6, 2001

(54) TETRAHYDROPYRIDO COMPOUNDS

(75) Inventors: Jörg Senn-Bilfinger; Gerhard Grundler, both of Constance (DE)

(73) Assignee: Byk Gulden Lomberg Chemische Fabrik GmbH, Constance (DE)

(*) Notice: Subject to any disclaimer, the term of this patent is extended or adjusted under 35 U.S.C. 154(b) by 0 days.

(21) Appl. No.: 09/381,617

(22) PCT Filed: Mar. 19, 1998

(86) PCT No.: PCT/EP98/01615

§ 371 Date: Sep. 24, 1999

§ 102(e) Date: Sep. 24, 1999

(87) PCT Pub. No.: WO98/42707

PCT Pub. Date: Oct. 1, 1998

(30) Foreign Application Priority Data

Mar. 24, 1997 (EP) .................................. 97104961
Oct. 30, 1997 (DE) .............................. 197 47 929

(51) Int. Cl.⁷ .................. A61K 31/4375; C07D 471/14; A61P 1/04
(52) U.S. Cl. ............................... 514/293; 546/82
(58) Field of Search ................. 546/82; 574/293

(56) References Cited

U.S. PATENT DOCUMENTS 4,468,400   8/1984   Gold et al. ........................... 424/256

FOREIGN PATENT DOCUMENTS 0 299 470   1/1989   (EP).
94/18199    8/1994   (WO).

Primary Examiner—Evelyn Mei Huang
(74) Attorney, Agent, or Firm—Jacobson, Price, Holman & Stern, PLLC

(57) ABSTRACT

Tetrahydropyrido compounds of formula (I)

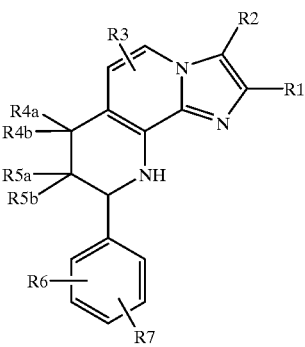

in which the substituents have the meanings mentioned in the description, are suitable for the prevention or treatment of gastrointestinal diseases.

14 Claims, No Drawings

TETRAHYDROPYRIDO COMPOUNDS

This application is the national phase of PCT/EP98/01615, filed Mar. 18, 1998.

RELATED APPLICATION

The subject matter disclosed and claimed herein is related to subject matter disclosed and claimed in copending application Ser. No. 09/582,212, filed Jul. 19, 2000.

FIELD OF APPLICATION OF THE INVENTION

The Invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines having various ring systems fused onto the imidazopyridine parent structure, which should be suitable for the treatment of peptic ulcer disorders.

DESCRIPTION OF THE INVENTION

The Invention relates to compounds of the formula I

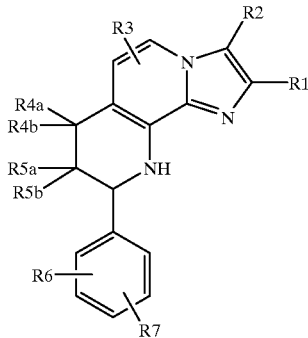

(I)

in which

R1 is 1–4C-alkyl,

R2 is 1–4C-alkyl or hydroxy-1–4C-alkyl,

R3 is hydrogen or halogen, one of the substituents R4a and R4b is hydrogen and the other is hydrogen, hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen, and the other substituents in each case together form a methylenedioxy radical (—O—CH$_2$—O—) or an ethylenedioxy radical (—O—CH$_2$—CH$_2$—O—), where R4a, R4b, R5a and R5b are not simultaneously hydrogen, R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl and R7 is hydrogen, halogen, 1–4C-alkyl or 1–4C-alkoxy, and their salts.

1–4C-alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical. The methyl radical is preferred.

Hydroxy-1–4C-alkyl represents abovementioned 1–4C-alkyl radicals which are substituted by a hydroxyl group. Examples which may be mentioned are the hydroxymethyl radical, the 2-hydroxyethyl radical and the 3-hydroxypropyl radical. The hydroxymethyl radical is preferred.

Halogen in the sense of the invention is bromine, chlorine or fluorine.

1–4C-alkoxy represents radicals which, in addition to the oxygen atom, contain a straight-chain or branched alkyl radical having 1 to 4 carbon atoms. Examples which may be mentioned are the butoxy radical, isobutoxy radical, sec-butoxy radical, tert-butoxy radical, propoxy radical, isopropoxy radical and preferably the ethoxy radical and methoxy radical.

1–4C-alkoxy-1–4C-alkoxy represents one of the abovementioned 1–4C-alkoxy radicals which is substituted by a further 1–4C-alkoxy radical. Examples which may be mentioned are the radicals 2-(methoxy)ethoxy (CH$_3$—O—CH$_2$—CH$_2$—O—) and 2-(ethoxy)ethoxy (CH$_3$—CH$_2$—O—CH$_2$—CH$_2$—O—).

1–4C-alkylcarbonyloxy represents a carbonyloxy group to which is bonded one of the abovementioned 1–4C-alkyl radicals. An example which may be mentioned is the acetoxy radical (CH$_3$CO—O—).

1–4C-alkoxycarbonyl represents a carbonyl group to which is bonded one of the abovementioned 1–4C-alkoxy radicals. Examples which may be mentioned are the methoxycarbonyl radical (CH$_3$O—C(O)—) and the ethoxycarbonyl radical (CH$_3$CH$_2$O—C(O)—).

1–4C-alkoxycarbonylamino represents an amino radical which is substituted by one of the abovementioned 1–4C-alkoxycarbonyl radicals. Examples which may be mentioned are the ethoxycarbonylamino radical and the methoxycarbonylamino radical.

1–4C-alkoxy-1–4C-alkoxycarbonyl represents a carbonyl group to which is bonded one of the abovementioned 1–4C-alkoxy-1–4C-alkoxy radicals. Examples which may be mentioned are the 2-(methoxy)ethoxycarbonyl radical (CH$_3$—O—CH$_2$CH$_2$—O—CO—) and the 2-(ethoxy)ethoxycarbonyl radical (CH$_3$CH$_2$—O—CH$_2$CH$_2$—O—CO—).

1–4C-alkoxy-1–4C-alkoxycarbonylamino represents an amino radical which is substituted by one of the abovementioned 1–4C-alkoxy-1–4C-alkoxycarbonyl radicals. Examples which may be mentioned are the 2-(methoxy)ethoxycarbonylamino radical and the 2-(ethoxy)ethoxycarbonylamino radical.

Suitable salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The compounds of the formula I have three chiral centers. The invention relates to all eight conceivable stereoisomer in any desired mixing ratio with one another, including the pure enantiomers, which are a preferred subject of the invention.

If one of the substituents R4a and R4b on the one hand and one of the substituents R5a and R5b on the other hand together form a methylenedioxy radical or ethylenedioxy radical, the two substituents which form the methylenedioxy radical or ethylenedioxy radical are preferably cis to one another.

Compounds to be emphasized are those of the formula I, in which

R1 is 1–4C-alkyl,

R2 is 1–4C-alkyl or hydroxy-1–4C-alkyl,

R3 is hydrogen, one of the substituents R4a and R4b is hydrogen and the other is hydrogen, hydroxyl or 1–4C-alkoxy, or in which R4a and R4b together are O (oxygen), one of the substituents R5a and R5b is hydrogen and the other is hydrogen, hydroxyl or 1–4C-alkoxy, or in which R5a and R5b together are O (oxygen), where R4a, R4b, R5a and R5b are not simultaneously hydrogen, R6 is hydrogen, halogen or trifluoromethyl and R7 is hydrogen or halogen, and their salts.

An embodiment of the invention to be emphasized are compounds of the formula I*

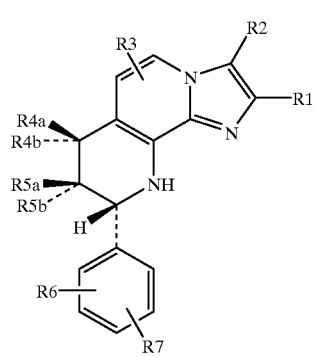

(I*)

in which

R1 is 1–4C-alkyl,

R2 is 1–4C-alkyl or hydroxy-1–4C-alkyl,

R3 is hydrogen, one of the substituents R4a and R4b is hydrogen and the other is hydrogen, hydroxyl or 1–4C-alkoxy, one of the substituents R5a and R5b is hydrogen and the other is hydrogen, hydroxyl or 1–4C-alkoxy, where R4a, R4b, R5a and R5b are not simultaneously hydrogen, R6 is hydrogen, halogen or trifluoromethyl and R7 is hydrogen or halogen, and their salts.

An embodiment of the invention particularly to be emphasized are compounds of the formula I*, in which R1 is 1–4C-alkyl, R2 is 1–4C-alkyl or hydroxymethyl, R3 is hydrogen, R4a is hydrogen, R4b is hydroxyl or 1–4C-alkoxy, R5a is hydrogen, hydroxyl or 1–4C-alkoxy, R5b is hydrogen, R6 is hydrogen, halogen or trifluoromethyl and R7 is hydrogen or halogen, and their salts.

A preferred embodiment of the invention are compounds of the formula I*, in which R1 is 1–4C-alkyl, R2 is 1–4C-alkyl, R3 is hydrogen, R4a is hydrogen, R4b is hydroxyl, R5a is hydroxyl, R5b is hydrogen, R6 is hydrogen, halogen or trifluoromethyl and R7 is hydrogen or halogen, and their salts.

With the aid of the general formula I*, the following exemplary compounds according to the invention may actually be mentioned by means of the substituent meanings and by the positions indicated for the substituents R3, R6 and R7 in the following Table 1 (Tab. 1):

TAB 1

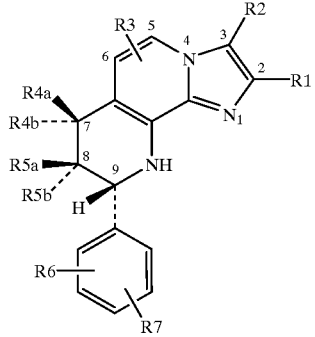
(I*)

| R1 | R2 | R3 | R4a | R4b | R5a | R5b | R6 | R7 |
|---|---|---|---|---|---|---|---|---|
| CH₃ | CH₃ | H | O | | H | H | H | H |
| CH₃ | CH₃ | H | H | OH | H | H | H | H |
| CH₃ | CH₃ | H | O | | H | H | 2-Cl | H |
| CH₃ | CH₃ | H | H | OH | H | H | 2-Cl | H |
| CH₃ | CH₃ | H | O | | H | H | 2-Cl | 6-Cl |
| CH₃ | CH₃ | H | H | OH | H | H | 2-Cl | 6-Cl |
| CH₃ | CH₃ | H | H | OCH₃ | H | H | H | H |
| CH₃ | CH₃ | H | H | OC₂H₅ | H | H | H | H |
| CH₃ | CH₃ | H | O | | H | H | 2-CF₃ | H |
| CH₃ | CH₃ | H | H | OH | H | H | 2-CF₃ | H |
| CH₃ | CH₃ | H | O | | OH | H | H | H |
| CH₃ | CH₃ | H | H | OH | OH | H | H | H |
| CH₃ | CH₃ | 6-Br | O | | H | H | H | H |
| CH₃ | CH₃ | 6-Br | H | OH | H | H | H | H |
| CH₃ | CH₃ | 6-Cl | H | OH | H | H | H | H |
| CH₃ | CH₃ | 6-Cl | H | OH | OH | H | H | H |
| CH₃ | CH₃ | H | H | OH | OH | H | 2-Cl | H |
| CH₃ | CH₃ | H | H | OH | OH | H | 2-Cl | 6-Cl |
| CH₃ | CH₃ | H | H | OH | OH | H | 4-Cl | H |
| CH₃ | CH₃ | H | H | OH | OH | H | 2-CF₃ | H |
| CH₃ | CH₃ | H | H | OH | OH | H | 2-NHCO—OCH₃ | 6-CH₃ |
| CH₃ | CH₃ | H | H | OH | OH | H | 2-NHCO—OC₂H₄—OCH₃ | 6-CH₃ |
| CH₃ | CH₂OH | H | O | | H | H | H | H |
| CH₃ | CH₂OH | H | H | OH | H | H | H | H |
| CH₃ | CH₂OH | H | O | | H | H | 2-Cl | H |
| CH₃ | CH₂OH | H | H | OH | H | H | 2-Cl | H |
| CH₃ | CH₂OH | H | O | | H | H | 2-Cl | 6-Cl |
| CH₃ | CH₂OH | H | H | OH | H | H | 2-Cl | 6-Cl |
| CH₃ | CH₂OH | H | H | OCH₃ | H | H | H | H |
| CH₃ | CH₂OH | H | H | OC₂H₅ | H | H | H | H |
| CH₃ | CH₂OH | H | O | | H | H | 2-CF₃ | H |
| CH₃ | CH₂OH | H | H | OH | H | H | 2-CF₃ | H |
| CH₃ | CH₂OH | H | O | | OH | H | H | H |
| CH₃ | CH₂OH | H | H | OH | OH | H | H | H |
| CH₃ | CH₂OH | 6-Br | O | | H | H | H | H |
| CH₃ | CH₂OH | 6-Br | H | OH | H | H | H | H |
| CH₃ | CH₂OH | 6-Cl | H | OH | H | H | H | H |
| CH₃ | CH₂OH | 6-Cl | H | OH | OH | H | H | H |
| CH₃ | CH₂OH | H | H | OH | OH | H | 2-Cl | H |
| CH₃ | CH₂OH | H | H | OH | OH | H | 2-Cl | 6-Cl |
| CH₃ | CH₂OH | H | H | OH | OH | H | 4-Cl | H |
| CH₃ | CH₂OH | H | H | OH | OH | H | 2-CF₃ | H |
| CH₃ | CH₂OH | H | H | OH | OH | H | 2-NHCO—OCH₃ | 6-CH₃ |
| CH₃ | CH₂OH | H | H | OH | OH | H | 2-NHCO—OC₂H₄—OCH₃ | 6-CH₃ | and the salts of the compounds mentioned in Table 1, the character "O" (=oxygen) between R4a and R4b in Table 1 denoting a 7-oxo compound.

The compounds according to the invention can thus be prepared as described by way of example in the following examples, or using analogous process steps starting from appropriate starting compounds The starting compounds are known or can be prepared analogously to the known compounds.

Depending on the substitution pattern in positions 7 and 8 (R4a/R4b or R5a/R5b), the compounds according to the invention can be prepared starting from N-protected 8-aminoimidazo[1,2-a]pyridines which are known or can be prepared in a known manner (see, for example, EP-A-0 299 470 or Kaminski et al., J. Med. Chem. 1985, 28, 876–892) according to the following reaction schemes:

Scheme 1

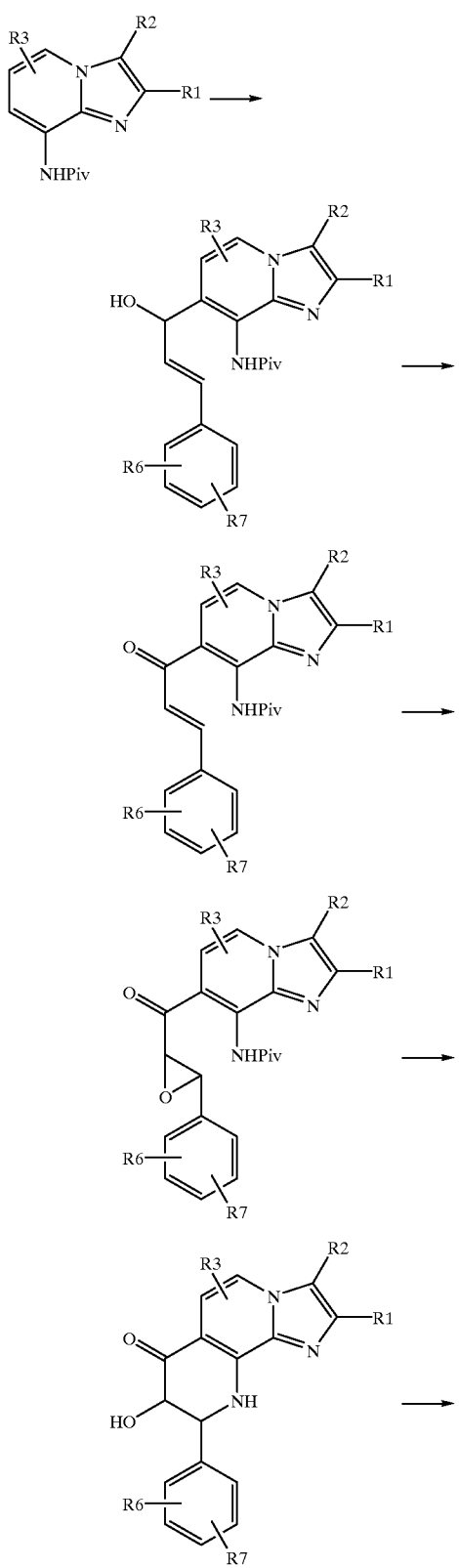

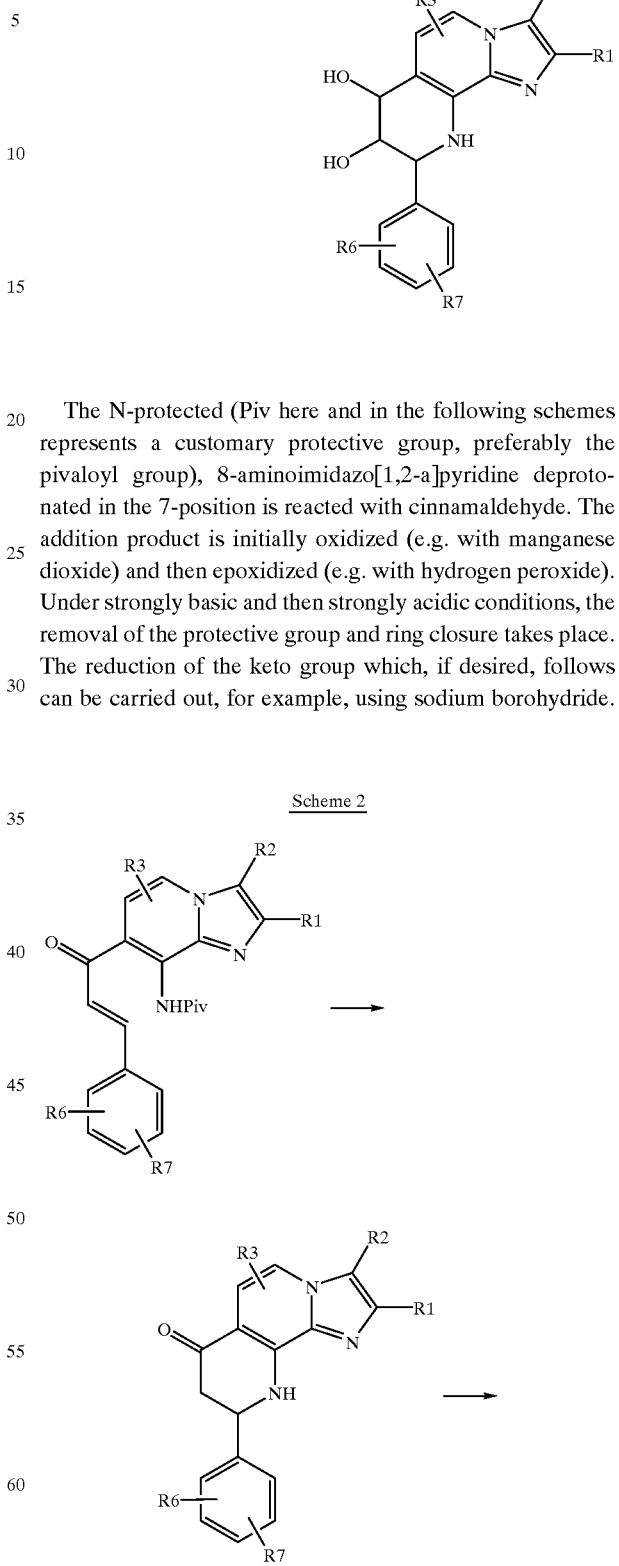

The N-protected (Piv here and in the following schemes represents a customary protective group, preferably the pivaloyl group), 8-aminoimidazo[1,2-a]pyridine deprotonated in the 7-position is reacted with cinnamaldehyde. The addition product is initially oxidized (e.g. with manganese dioxide) and then epoxidized (e.g. with hydrogen peroxide). Under strongly basic and then strongly acidic conditions, the removal of the protective group and ring closure takes place. The reduction of the keto group which, if desired, follows can be carried out, for example, using sodium borohydride.

Scheme 2

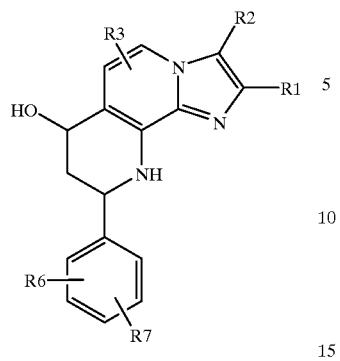

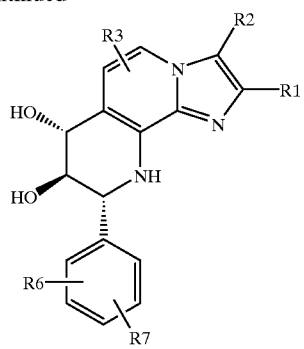

Instead of the epoxidation according to Scheme 1, the protective group is removed and the ring is closed under strongly acidic conditions. The reduction to the alcohol which, if desired, follows is carried out by means of sodium borohydride.

The above scheme represents an example of an enantioselective synthesis, the same N-protected imidazo[1,2-a] pyridines being used as starting materials as in Scheme 1. The reaction of these imidazo[1,2-a]pyridines in deprotonated form with enantiomerically pure dioxolanes initially leads to a condensation product which can be cyclized under strongly acidic conditions with removal of the protecting groups. The subsequent reduction of the keto group using sodium borohydride (also see Scheme 1) leads in over 90% enantiomeric purity to the final product indicated.

Scheme 3

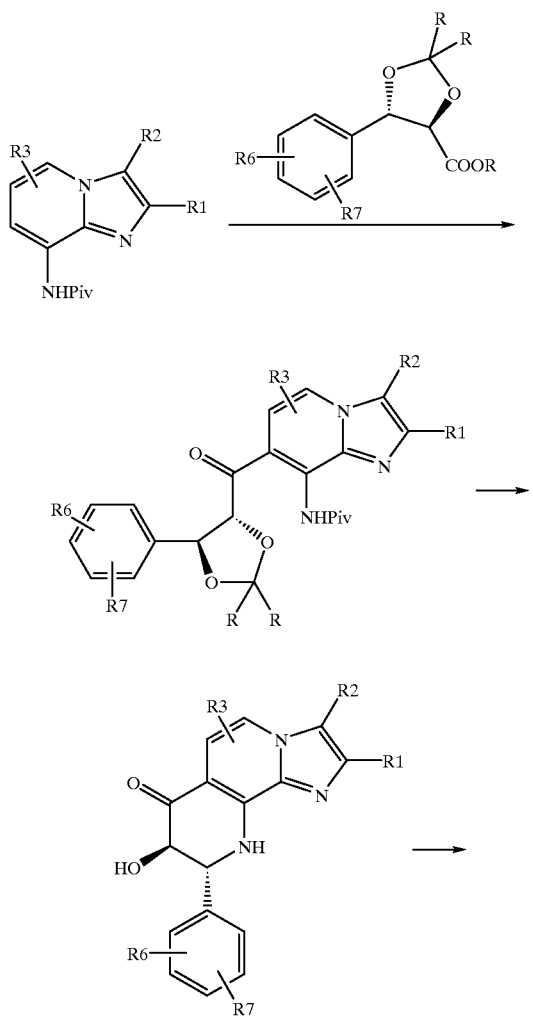

Scheme 4

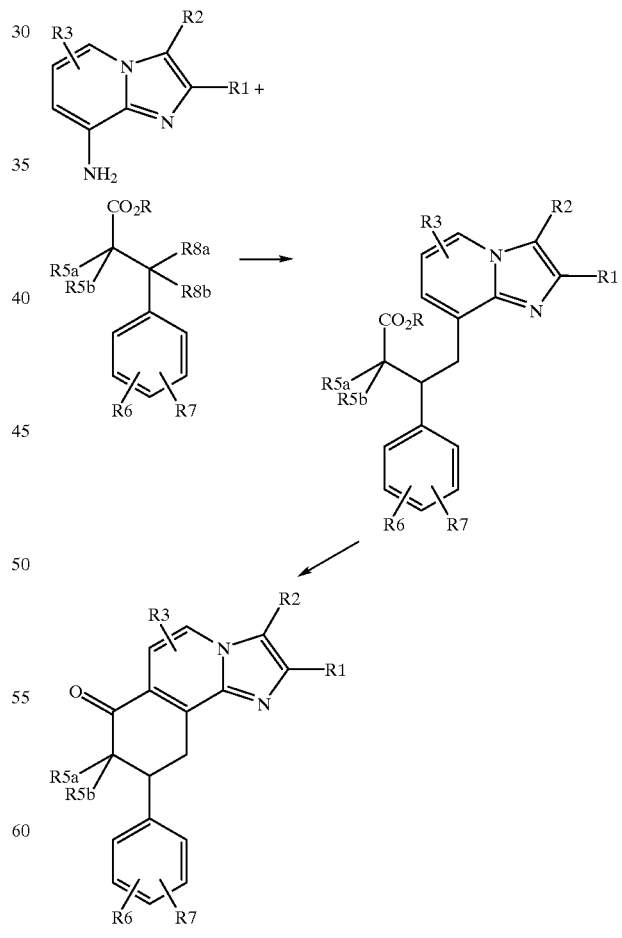

Starting from the abovementioned 8-aminoimidazo[1,2-a]pyridines, the compounds substituted on the 8-amino group are obtained either by alkylation using suitable alkylating agents bearing substituents (e.g. R8a=hydrogen, R8b=halogen), or by reductive alkylations with appropriately substituted ketones [R8a and R8b together are O (oxygen)] with the aid of reductants such as sodium cyanoborohydride and these are ring-closed under base or acid catalysis to give the cyclic ketones, which for their part can be converted into the desired target compounds by suitable chemical transformations (see, for example, Schemes 1 and 2). If necessary, the group $CO_2R$ can also be initially reduced (aldehyde stage) before the cyclization, 7-hydroxy-substituted derivatives then being formed, which for their part can be converted into suitable target compounds by oxidation/reduction.

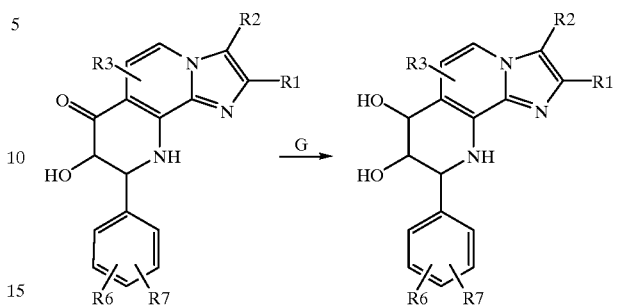

In a variant of the process outlined above in Scheme 4 where R5a and R8a =H (hydrogen) and R5b and R8b together =O (oxygen), the 8-aminoimidazo[1,2-a]pyridine is initially reacted with epoxycinnamic acid ester derivatives with regioselective epoxide opening (A). The products are cyclized under aprotic basic conditions (C). Alternatively to this, the mixture can be hydrolysed and the free carboxylic acid derivative cyclized under acidic conditions (D). In both cases, the keto group can then be reduced to the alcohol (G), as outlined in Scheme 1, for example using sodium borohydride. If the 8-aminoimidazo[1,2-a]pyridine is reacted with protected epoxycinnamaldehyde derivatives (B) the products can be ring-closed under acidic conditions after removal of the acetal protective group (F). A reduction of the ester function to the aldehyde and an acidic cyclization are likewise possible (E). Both the reduction of the keto function and the ring closure at the aldehyde stage can be carried out enantioselectively, such that when using the corresponding enantiomerically pure epoxy derivatives an enantioselective synthesis is possible.

Scheme 5

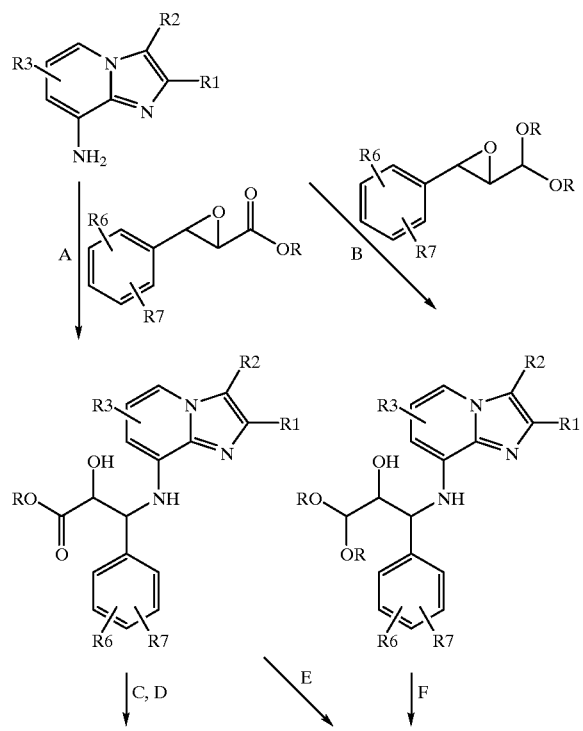

Scheme 6

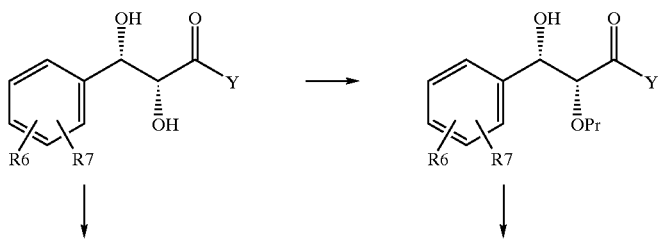

-continued
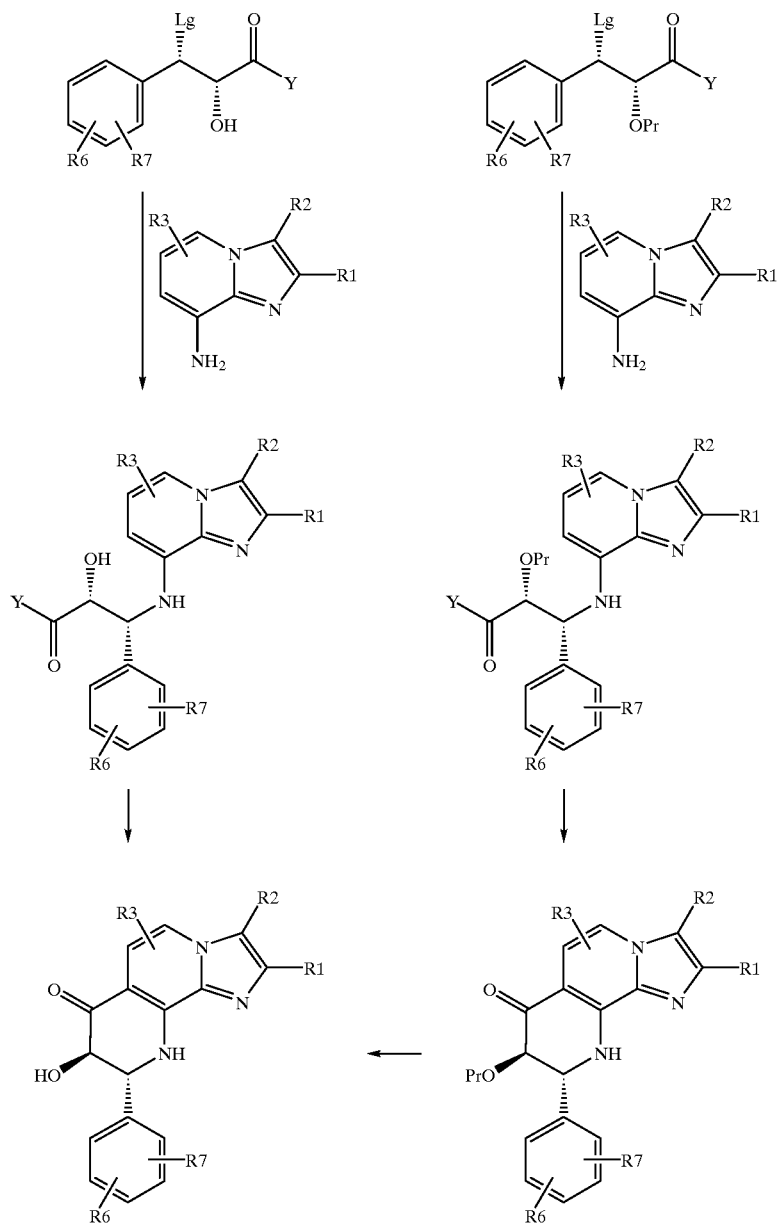
Pr = protective group
Lg = leaving group
Y = H, OR, NR$_2$, halogen etc.

In a further variant of Scheme 4, an enantioselective synthesis is outlined above. The dihydroxycinnamic acid derivative is activated in the benzylic position either directly or after introduction of a protective group on the second hydroxyl group. The products thus obtained are reacted with the 8-aminoimidazo[1,2-a]pyridine. Ring closure is then carried out,. e.g. under basic conditions. The step (reduction) which, if desired, then follows is carried out analogously to Scheme 3.

Scheme 7

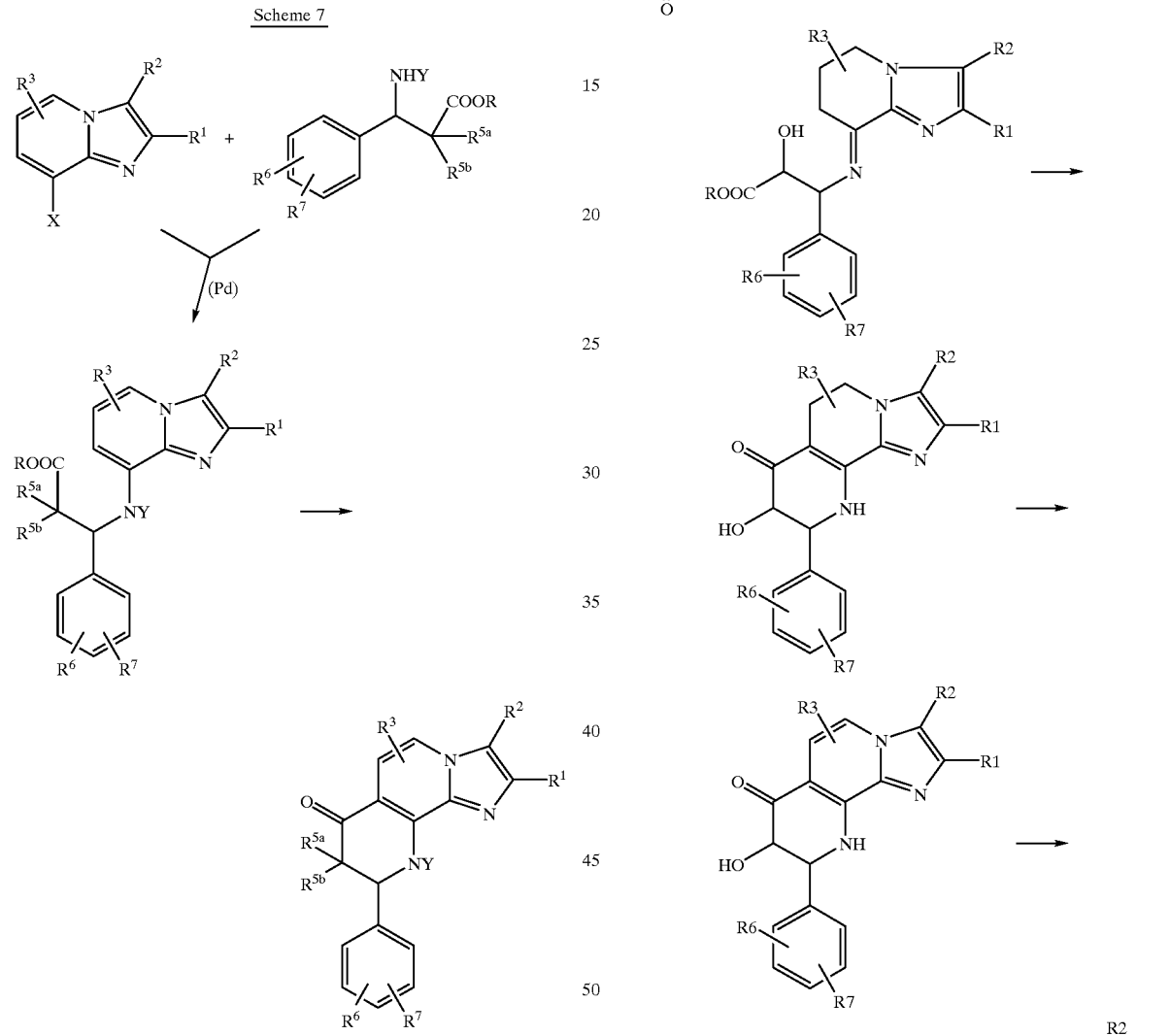

8-Haloimidazo[1,2-a]pyridines (X=halogen) are reacted with suitably substituted β-phenyl-β-amino acids with heavy metal catalysis (Pd preferred) to give the substituted amines, which for their part are cyclized according to Scheme 4. Instead of the COOR group, the aldehyde group can also be used (as already mentioned in Scheme 4), if desired in the form of the acetal. Y is H (hydrogen) or a protective group which can be removed before or after ring closure.

Starting from the imidazole which is known or can be prepared in an analogous manner, the ring closure to be effected (optionally under protection of the hydroxy group) is favored by the presence of an enamine structure (equilibrium!). After the introduction of the double bond by oxidation, the reduction of the keto group to the alcohol can be carried out as outlined in Scheme 1.

In the above schemes, "R" is 1–4C-alkyl, in the ester groups mentioned by way of example (—COOR or —CO₂R), there can be another leaving group instead of the radical —OR or there can also be another group which can be used as far as its functionality is concerned instead of the ester group.

Compounds of the formula I in which R4a/R4b or R5a/R5b are 1–4C-alkoxy, 1–4C-alkoxy-1-4C-alkoxy or 1–4C-alkylcarbonyloxy can be prepared by customary derivatization measures, such as are familiar to the person skilled in the art (e.g. by alkylation or by acylation), from the corresponding compounds in which R4a/R4b or R5a/R5b are hydroxyl.

Compounds of the formula I in which R2 is hydroxy-1–4C-alkyl or the corresponding starting compounds of the Schemes 1 to 8 can be produced from the corresponding esters and aldehydes by reduction, for example with sodium borohydride or lithium aluminium hydride, in a customary manner (cf. WO 94/18199). If desired, the reduction for obtaining the hydroxy-1–4C-alkyl group can be accomplished simultaneously with the reduction of the keto group in position 8 and in particular in position 7 (R4a and R4b together are O).

The substances according to the invention are isolated and purified in a manner known per se, for example, by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methyl chloride or chloroform, or a low molecular weight aliphatic alcohol (ethanol, isopropanol) which contains the desired acid, or to which the desired acid is subsequently added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The pure enantiomers, in particular the pure enantiomers of the formula I*, to which the invention preferably relates, can be obtained in a manner familiar to the person skilled in the art, for example by enantioselective synthesis (see, for example, Scheme 3), by chromatographic separation on chiral separating columns, by derivatization with chiral auxiliary reagents, subsequent separation of diastereomers and removal of the chiral auxiliary group, by salt formation with chiral acids, subsequent separation of the salts and liberation of the desired compound from the salt, or by (fractional) crystallization from a suitable solvent.

The invention further relates to the processes and the process intermediates described in the above schemes, in particular those process intermediates of Schemes 1, 2, 3, 4, 5, 6 and 7, which can be isolated before the cyclization step.

The following examples serve to illustrate the invention further without restricting it. Likewise, further compounds of the formula I whose preparation is not described explicitly can be prepared analogously or in a manner familiar to the person skilled in the art using customary process techniques. The abbreviation min stands for minute(s), h for hour(s) and ee for enantiomeric excess.

EXAMPLES

Final Products 1. 2,3-Dimethyl-9-phenyl-7,8,9,10-tetrahydroimidazo[1,2-h][1,7]naphthyridin-7-one A solution of 4.5 g of 2,3-dimethyl-7-(3-phenyl-1-oxo-2-propenyl)-8-pivaloyl-aminoimidazo[1,2-a]pyridine in 30 ml of dioxane is treated with 20 ml of conc. hydrochloric acid, refluxed for 8 h, adjusted to pH 7.0 with 2N sodium hydroxide solution with cooling and extracted three times with 50 ml of ethyl acetate. The combined extracts are washed with water, dried over potassium carbonate and concentrated to dryness in vacuo. The residual viscous oil is chromatographed on silica gel using ethyl acetate/petroleum ether (1:1) as an eluent. 2.6 g of the title compound of melting point 138–40° C. are obtained.

2. 9-(2-Chlorophenyl)-2,3-dimethyl-7,8,9,10-tetrahydroimidazo[1,2-h][1,7]naphthyridin-7-one The title compound of melting point 80–2° C. is obtained from 7-[3-(2-chlorophenyl)-1-oxo-2-propenyl]-8-pivaloylamino-2,3-dimethylimidazol[1,2-a]pyridine in 73% yield analogously to Example 1.

3. 9-(2,6-Dichlorophenyl)-2,3-dimethyl-7,8,9,10-tetrahydroimidazo[1,2-h][1,7]naphthyridin-7-one The title compound of melting point 248–9° C. is obtained from 7-[3-(2,6-dichlorophenyl)-1-oxo-2-propenyl]-8-pivaloylamino-2,3-dimethylimidazol[1,2-a]pyridine in 41% yield analogously to Example 1.

4. 9-(2-Trifluoromethylphenyl)-2,3-dimethyl-7,8,9,10-tetrahydroimidazo[1,2-h][1,7]naphthyridin-7-one The title compound of melting point 184–5° C. is obtained from 7-[3-(2-trifluoromethylphenyl)-1-oxo-2-propenyl]-8-pivaloylamino-2,3-dimethylimidazol[1,2-a]pyridine in 41% yield analogously to Example 1.

5. 7-Hydroxy-2,3-dimethyl-9-phenyl-7,8,9,10-tetrahydroimidazo[1,2-h][1,7]naphthyridine A suspension of 1 g of 2,3-dimethyl-9-phenyl-7,8,9,10-tetrahydroimidazo[1,2-h][1,7]naphthyridin-7-one in 15 ml of methanol is treated at room temperature with 450 mg of sodium borohydride in small portions. The resulting yellowish solution is stirred for 2 h and then diluted with ice water. The precipitate which is deposited is filtered off with suction and washed with a little cold 2-propanol. 800 mg of the title compound of melting point 210–12° C. are obtained.

6. 9-(2-Chlorophenyl)-7-hydroxy-2,3-dimethyl-7,8,9,10-tetrahydroimidazo[1,2-h][1,7]-naphthyridine The title compound of melting point 150–2° C. is obtained from 9-(2-chlorophenyl)-2,3-dimethyl-7,8,9,10-tetrahydroimidazo[1,2-h][1,7]naphthyridin-7-one in 73% yield analogously to Example 5.

7. 9-(2,6-Dichlorophenyl)-7-hydroxy-2,3-dimethyl-7,8,9,10-tetrahydroimidazo[1,2-h][1,7]-naphthyridine The title compound of melting point 155–7° C. is obtained from 9-(2,6-dichlorophenyl)-2,3-dimethyl-7,8,9,10-tetrahydroimidazo[1,2-h][1,7]naphthyridin-7-one in 72% yield analogously to Example 5.

8. 9-(2-Trifluoromethylphenyl)-7-hydroxy-2,3-dimethyl-7,8,9,10-tetrahydroimidazo[1,2-h][1,7]-naphthyridine The title compound of melting point 145–7° C. is obtained from 9-(2-trifluoromethylphenyl)-2,3-dimethyl-7,8,9,10-tetrahydroimidazo[1,2-h][1,7]-naphthyridin-7-one in 72% yield analogously to Example 5.

9. 8-Hydroxy-2,3-dimethyl-9-phenyl-7,8,9,10-tetrahydroimidazo[1,2-h][1,7]naphthyridin-7-one A solution of 500 mg of 2,3-dimethyl-7-(2,3-epoxy-1-oxo-3-phenylpropyl)-8-pivaloyl-aminoimidazo[1,2-a]

pyridine in 5 ml of dry ethanol is treated with vigorous stirring with 95 mg of lithium hydroxide and, after stirring at room temperature for 2 hours, cooled to 0° C. in an ice bath. The crystals which are deposited are filtered off with suction and washed with a little cold ethanol. After drying in a high vacuum, the solid is introduced into 5 ml of 90% strength sulfuric acid at room temperature and stirred for 1 h. It is then neutralized with 40% strength cooled sodium hydroxide solution with ice cooling. The precipitate which is deposited in this process is filtered off and dried in vacuo. 145 mg of the title compound of melting point 232–4° C. are obtained.

10. 7,8-Dihydroxy-2,3-dimethyl-9-phenyl-7,8,9,10-tetrahydroimidazo[1,2-h][1,7]naphthyridine 700 mg of 8-hydroxy-2,3-dimethyl-9-phenyl-7,8,9,10-tetrahydroimidazo[1,2-h][1,7]-naphthyridin-7-one are suspended in 15 ml of methanol and treated with 200 mg of sodium borohydride in portions at room temperature with stirring. After stirring for 2 hours, the mixture is poured onto 100 ml of ice water. The precipitate which is deposited is filtered off, briefly dried in vacuo and recrystallized from a little 2-propanol. 500 mg of the title compound of melting point 150–2° C. are obtained.

11. (8R,9R)-2,3-Dimethyl-8-hydroxy-9-phenyl-7,8,9,10-tetrahydroimidazo[1,2-h][1,7]naphthyridin-7-one 10.8 g (24 mmol) of 2,3-dimethyl-7-[(2S,3R)-2,3-O-isopropylidene-3-phenylpropan-1-on-1-yl]-8-pivaloylaminoimidazo[1,2-a]pyridine (ee>95%, Daicel Chiralcel HPLC) are introduced into 50 ml of 70% strength sulfuric acid with ice cooling during the course of 4 min. A suspension is formed in the course of this, which turns into an orange solution after 30 min. After addition is complete, the ice bath is removed and the mixture is stirred on at room temperature. The reaction solution is added after 50 h to ice water and dichloromethane is added, then the mixture is adjusted to pH 8 using 6N sodium hydroxide solution and saturated sodium hydrogen-carbonate solution. The organic phase is separated off. The aqueous phase is extracted twice with dichloromethane. The organic phases are combined and washed with a little distilled water. The organic layer is then dried over anhydrous sodium sulfate, filtered and concentrated on a vacuum rotary evaporator. The concentrated residue is chromatographed on silica gel (eluent: dichloromethane/methanol 100/1). The main fraction is concentrated and treated with ethyl acetate, and the title compound crystallizes in the course of this as a yellow solid. This precipitate is filtered off with suction and dried to constant weight in a vacuum drying oven at 50° C. 4.22 g (57%, ee>95%, Daicel Chiralcel HPLC) of the title compound of melting point 231–4° C. are obtained.

12. (7R,8R,9R)-2,3-Dimethyl-7,8-dihydroxy-9-phenyl-7,8,9,10-tetrahydroimidazo[2h][1,7]-napthyridine 6 g (19.52 mmol) of (8R,9R)-2,3-dimethyl-8-hydroxy-9-phenyl-7,8,9,10-tetrahydroimidazo[1,2-h][1,7] naphthyridin-7-one (ee>90%, Daicel Chiralcel HPLC) are suspended in 60 ml of methanol and cooled to –5° to 0° C. in a methanol-ice bath. At this temperature, sodium borohydride (0.81 g, 21.47 mmol) is added by spatula during the course of 0.5 h (evolution of gas). After addition is complete, the mixture is stirred for a further 10 min, and then concentrated in a vacuum rotary evaporator at a bath temperature of 40° C. The oily residue obtained is taken up in distilled water and extracted three times with chloroform. The organic phases are combined and washed with a little water, then dried using anhydrous sodium sulfate and filtered. The filtrate is concentrated on a vacuum rotary evaporator and co-evaporated with acetone; the title compound crystallizes out in the course of this. The precipitate is filtered off, washed with acetone and dried to constant weight at 50° C. in a vacuum drying oven. 5.15 g (85.3%, ee>90%, Daicel Chiralcel HPLC) of the title compound are obtained as a colorless crystallizate of melting point 206–9° C.

13. (7S,8R,9R)-2,3-Dimethyl-7,8-dihydroxy-9-phenyl-7,8,9,10-tetrahydro-imidazo[1,2-h][1,7]naphthyridine 2 g of the mother liquor of example 12 are chromatographed on silica gel (eluent: ethyl acetate/methanol 19/1) to give 0.35 g of the title compound as an oil which crystallizes upon addition of ethyl acetate. Melting point: 199–200° C. (ethyl acetate).

14. (8R,9R)-3-Formyl-8-hydroxy-2-methyl-7-oxo-9-phenyl-7,8,9,10tetrahydroimidazo[1,2-h][1,7]naphthyridine (8R,9R)-8-hydroxy-2,3-dimethyl-7-oxo-9-phenyl-7,8,9,10-tetrahydroimidazo[1,2-h][1,7]naphthyridine (1 g) is dissolved in 20 ml of dried chloroform, and 5 g of potassium permanganate was added. After stirring the reaction mixture at room temperature for 40 days, the solids are filtered off. The filtrate is chromatographed twice on silica gel (eluents: dichloromethane/methanol 13/1) to give 0.07 g of the title compound as a semisolid.

15. (7R,8R,9R)-3-Hydroxymethyl-7,8-dihydroxy-2-methyl-9-phenyl-7,8,9,10-tetrahydro-imidazo[1,2-h][1,7] naphthyridine 0.07 g of (8R,9R)-3-formyl-8-hydroxy-2-methyl-7-oxo-9-phenyl-7,8,9,10-tetrahydro-imidazo[1,2-h][1,7] naphthyridine are dissolved in 5 ml of dry methanol, and 0.1 g of sodium borohydride is added. The mixture is stirred for 30 min and concentrated in vacuo. The oily residue is partitioned between water and chloroform. The organic layer is separated, dried over anhydrous sodium sulfate and concentrated. The product is purified by flash chromatography on silica gel (eluent: dichloromethane/methanol 9/1) to give 0.05 g of the title compound as a semi solid.

1H-NMR (CD3OH, 400 MHz) δ=1.90 (s, 3H, 2-CH3), 3.87 (dd, J8.9=9.5 Hz, J8,7=8.0 Hz, 1H, 8-H), 4.45 (d, J9,8=9.4 Hz, 1H, 9-H), 4.79 (bs, 2H, 3-CH2)5.42 (d,J7,8= 8.0 Hz, 1H, 7-H), 7.03 (d, J6,5 =6.9Hz, 1H, 6-H), 7.35–7.42 (m, 3H 9Ph), 7.55 (d, J=7.0 Hz, 2H, 9-Ph), 7.77 (d, J5,6=7.0 Hz, 1H, 5-H).

16. (7S,8R,9R)-7,8-ispropylidenedioxy-2,3-dimethyl-9-phenyl-7,8,9,10-tetrahydro-imidazo[1,2-h][1,7] naphthyridine 0.3 g of (7S,8R,9R)-2,3-dimethyl-7,8-dihydroxy-9-phenyl-7,8,9,10-tetrahydroimidazo-[1,2-h][1,7] naphthyridine are dissolved in 5 ml of dry acetone and 10 ml of dry N,N-dimethyl formamide. 2,2-Dimethoxypropane (20 ml) and p-toluenesulfonic acid monohydrate (0.68 g) are added, and the mixture is stirred for 20 h at room temperature. The reaction mixture is partitioned between water and dichloromethane. The organic layer is separated, washed with water and dried over anhydrous sodium sulfate. After evaporation of the solvent, the residue is chromatographed on silica gel (eluent: ethyl acetate/methanol 20/1) to give 0.2 g of the title compound as colourless needles, melting point: 231–232° C. (dec., diethyl ether).

Starting Compounds

A. 2,3-Dimethyl-7-(3-phenyl-1-oxo-2-propenyl)-8-pivaloylaminoimidazo[1,2-a]pyridine Method A a) 7-Tributylstannyl-2,3-dimethyl-8-pivaloylaminoimidazo [1,2-a]pyridine A solution of 1 g of 2,3-dimethyl-8-pivaloylaminoimidazo[1,2-a]pyridine in 40 ml of diethyl ether is treated dropwise at –78° C. with 8 ml of a 1.5 molar solution of t-butyllithium in n-pentane. The mixture is stirred for 15 min and then treated with 3.3 ml of tri-n-butyltin chloride. The internal temperature is then allowed to rise to room temperature, the mixture is poured onto ice water and extracted three times with ethyl acetate, the combined extracts are washed with a little water and dried over potassium carbonate, the solvent is stripped off in vacuo and the oil obtained is chromatographed on silica gel using ethyl acetate/petroleum ether (1:3) as an eluent. 1.3 g of 7-tributylstannyl-2,3-dimethyl-8-pivaloylaminoimidazo [1,2-a]pyridine are obtained as a viscous oil.

b) 2,3Dimethyl-7-(3-phenyl-1-oxo-2-propenyl)-8-pivaloylaminoimidazo[1,2-a]pyridine A solution of 1 g of 7-tributylstannyl-2,3-dimethyl-8-pivaloylaminoimidazo[1,2-a]pyridine in 15 ml of tetrahydrofuran is treated successively with 85 mg of lithium chloride, 60 mg of bis(acetonitrile)palladium(II) chloride and 340 mg of cinnamoyl chloride. The mixture is stirred at 60° C. for 3 h. The yellowish precipitate is filtered off with suction after cooling to 0° C. and washed with a little tetrahydrofuran and diethyl ether. After drying in vacuo, 720 mg of the title compound are obtained as the hydrochloride salt of melting point 263–5° C. (with decomposition).

Method B a) 2,3-Dimethyl-7-(3-phenyl-1-hydroxy-2-propenyl)-8-pivaloylaminoimidazo[1,2-a]pyridine A vigorously stirred solution of 41 g of 8-pivaloylamino-2,3-dimethylimidazo[1,2-a]pyridine is treated dropwise at −78° C. under argon protective gas with 320 ml of a commercially available, 1.5 molar solution of t-butyllithium in n-pentane such that the temperature does not exceed −70° C. After stirring at −78° C. for a further 15 min, a solution of 61 g of cinnamaldehyde in 50 ml of dry diethyl ether is added dropwise (internal temperature <−68° C.). The mixture is then allowed to warm to room temperature, and is poured cautiously onto ice water and extracted three times with a total of 500 ml of ethyl acetate, the reddish-colored, organic phase is washed with distilled water and dried over sodium sulfate, and the solvent is stripped off in vacuo. The residual, yellowish suspension is treated with diethyl ether. The crystals obtained are filtered off with suction. 30 g of 2,3-dimethyl-7-(3-phenyl-1-hydroxy-2-propenyl)-8-pivaloylaminoimidazo[1,2-a]pyridine of melting point 194–5° C. are obtained.

b) 2,3-Dimethyl-7-(3-phenyl-1-oxo-2-propenyl)-8-pivaloylaminoimidazo[1,2-a]pyridine A solution of 35.5 g of 2,3-dimethyl-7-(3-phenyl-1-hydroxy-2-propenyl)-8-pivaloylaminoimidazo[1,2-a] pyridine in 900 ml of trichloromethane is treated with 60 g of manganese dioxide and stirred vigorously at room temperature for 20 h. The mixture is then filtered, the filtrate is concentrated to dryness in vacuo and the oil obtained is treated with a little diisopropyl ether. The crystals obtained in this process are filtered off with suction. 31.5 g of the title compound of melting point 108–10° C. are obtained.

B. 7-[3-(2-Chlorophenyl)-1-oxo-2-propenyl]-8-pivaloylamino-2,3-dimethylimidazo[1,2-a]pyridine The title compound of melting point 158–60° C. is obtained in 42% yield as the hydrochloride analogously to Example A, method A, by corresponding reaction with 2-chlorocinnamoyl chloride.

C. 7-[3-(2,6-Dichlorophenyl)-1-oxo-2-propenyl]-8-pivaloylamino-2,3-dimethylimidazo[2-a]pyridine The title compound of melting point 218–19° C. is obtained in 51% yield as the hydrochloride analogously to Example A, method A, by corresponding reaction with 2,6-dichlorocinnamoyl chloride.

D. 7-[3-(2-Trifluoromethyphenyl)-1-oxo-2-propenyl]-8-pivaloylamino-2,3-dimethylimidazo[1,2-a]pyridine The title compound of melting point 206–8° C. is obtained in 12% yield as the hydrochloride analogously to Example A, method A, by corresponding reaction with 2-trifluoromethylcinnamoyl chloride.

E. 2,3-Dimethyl-7-(2,3-epoxy-1-oxo-3-phenylpropyl)-8-pivaloylaminoimidazo[1,2-a]pyridine A mixture of 4 g of 2,3-dimethyl-7-(3-phenyl-1-oxo-2-propenyl)-8-pivaloyl-aminoimidazo[1,2-a]pyridine in 60 ml of acetone and 400 mg of sodium hydroxide in 12 ml of water is treated dropwise with vigorous stirring at 30° C. with 5.6 ml of commercially available, 30% strength aqueous hydrogen peroxide (20 min). After stirring at 30° C. for a further 30 minutes, the mixture is cooled to 0° C. and treated with a mixture of 60 ml of water, 13 g of sodium thiosulfate and 30 ml of ethyl acetate. After phase separation, the aqueous phase is extracted with 20 ml of ethyl acetate. The organic phases are combined, washed with a little water and dried over potassium carbonate. After stripping off the solvent in vacuo, the residual oil is dried in a high vacuum. 4 g of the title compound are obtained as an amorphous mass.

F. 2,3-Dimethyl-7-[(2S,3R)-2,3-O-isopropylidene-3-phenylpropan-1-on-1-yl]-8-pivaloylaminoimidazo[1,2-a] pyridine 60 g (0.245 mol) of 2,3-dimethyl-8-pivaloylaminoimidazo[1,2-a]pyridine are dissolved in 1.5 l of anhydrous diethyl ether with exclusion of moisture and under an argon athmosphere and cooled to −75° C. By means of a flex needle, 408 ml (0.612 mol) of tert-butyllithium solution (1.5 M in n-pentane) are added dropwise such that the temperature does not exceed −65° C. (30 min). A red suspension is formed. After addition is complete, the suspension is stirred at −75° C. for a further 30 min. ⅓ of a solution of 145 g of methyl (2S,3R)-2,3-O-isopropylidene-3-phenylpropionate (ee: 99.05%, Daicel Chiralcel HPLC) in 150 ml of absolute THF is then slowly added dropwise at a temperature of below −65° C. during the course of 30 min. The residual quantity is then briskly added dropwise (5 min), a temperature rise to −60° C. taking place. After addition is complete the cooling bath is removed. On reaching an internal temperature of −30° C., 20 ml of methanol are added and at an internal temperature of 0° C. 200 ml of distilled water are added. The aqueous phase is separated off in a separating funnel, the organic phase is washed five times with 100 ml of distilled water each time, then the organic phase is extracted three times with 10% strength sulfuric acid (200 ml, 50 ml, 50 ml). The sulfuric acid phases are combined, treated with 200 ml of dichloromethane and adjusted to pH 2.3 with 10N sodium hydroxide solution and with ice cooling and vigorous stirring. The organic phase is separated off. The aqueous phase is extracted with 30 ml of dichloromethane. The combined dichloromethane phases are washed twice with a little distilled water. The organic phase is then dried over anhydrous sodium sulfate and the solvent is completely stripped off in vacuo. A brown oil is obtained which is treated with 50 ml of diethyl ether. After seeding, crystals are formed which are filtered off after standing overnight and washed with diethyl ether. After drying in vacuo, 57.7 g (52.5%, ee>99%, Daicel Chiralcel HPLC) of the title compound of melting point 76–80° C. are obtained as a pale yellow powder.

Commercial Utility

The compounds of the formula I and their salts have useful pharmacological properties which make them commercially utilizable. In particular, they exhibit a marked inhibition of gastric acid secretion and an excellent gastric and intestinal protective action in warm-blooded animals, in particular humans. In this context, the compounds according to the invention are distinguished by a high selectivity of action, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions (such as, for example, stomach ulcers, duodenal ulcers, gastritis, hyperacidic or medicament-related functional gastropathy), which can be caused, for example, by microorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula I and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention furthermore relates to medicaments which contain one or more compounds of the formula I and/or their pharmacologically tolerable salts.

The medicaments are prepared by processes known per se, which are familiar to the person skilled in the art. As medicaments, the pharmacologically active compounds according to the invention (=active compounds) are employed either as such, or preferably in combination with suitable pharmaceutical auxiliaries or excipients in the form of tablets, coated tablets, capsules, suppositories, patches (e.g. as TTS), emulsions, suspensions or solutions, where the active compound content is advantageously between 0.1 and 95% and where, by the appropriate choice of the auxiliaries and excipients, a pharmaceutical administration form (e.g. a delayed-release form or an enteric form) exactly suited to the active compound and/or to the desired onset of action can be achieved.

The person skilled in the art is familiar, on the basis of his expert knowledge, with auxiliaries or excipients which are suitable for the desired pharmaceutical formulations. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose from approximately 0.01 to approximately 20, preferably 0.05 to 5, in particular 0.1 to 1.5, mg/kg of body weight, If appropriate in the form of several, preferably 1 to 4, individual doses to achieve the desired result. In the case of parenteral treatment, similar or (in particular in the case of intravenous administration of the active compounds), as a rule, lower doses can be used. The optimal dose and manner of administration of the active compounds necessary in each case can easily be determined by any person skilled in the art on the basis of his expert knowledge.

If the compounds according to the invention and/or their salts are to be employed for the treatment of the abovementioned diseases, the pharmaceutical preparations can also contain one or more pharmacologically active constituents of other pharmaceutical groups. Examples which may be mentioned are: tranquilizers (for example from the benzodiazapines group, e.g. diazepam), spasmolytics (e.g. bietamiverine or camylofin), anticholinergics (e.g. oxyphencyclimine or phencarbamide), local anesthetics (e.g. tetracaine or procaine), and, if appropriate, also enzymes, vitamins or amino acids.

To be emphasized in this connection, in particular, is the combination of the compounds according to the invention with pharmaceuticals which inhibit acid secretion, such as, for example, H2 blockers (e.g. cimetidine, ranitidine), H+/K+−ATPase inhibitors (e.g. omeprazole, pantoprazole), or furthermore with so-called peripheral anticholinergics (e.g. pirenzepine, telenzepine), and with gastrin antagonists with the aim of increasing the main action in an additive or superadditive sense and/or of eliminating or decreasing the side effects, or furthermore the combination with antibacterially active substances (e.g. cephalosporins, tetracyclines, penicillins, macrolides, nitroimidazoles or alternatively bismuth salts) for the control of Helicobacter pylori. Antibacterially active combination components which may be mentioned are, for example, meziocillin, ampicillin, amoxycillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric acid secretion-inhibiting action of the compounds according to the invention can be demonstrated in animal experimental models. The compounds according to the invention investigated in the model mentioned below have been provided with numbers which correspond to the numbers of these compounds in the examples.

Testing of the Secretion-inhibiting Action on the Perfused Rat Stomach

Table A below shows the effects of the compounds according to the invention on the pentagastrin-stimulated acid secretion of the perfused rat stomach in vivo after intravenous administration.

TABLE A

| No. | Dose ($\mu$mol/kg) I.v. | Inhibition of acid secretion (%) |
|---|---|---|
| 5 | 3 | 100 |
| 6 | 3 | 100 |
| 10 | 3 | 100 |

TABLE A-continued

| No. | Dose (μmol/kg) I.v. | Inhibition of acid secretion (%) |
|---|---|---|
| 12 | 3 | 100 |
| 13 | 3 | 100 |

Methodology

The abdomen of anesthetized rats (CD rat, female, 200–250 g; 1.5 g/kg i.m. urethane) was opened after tracheotomy by means of a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm physiological NaCl solution at 37° C. was continuously passed through the stomach (0.5 ml/min, pH 6.8–6.9; Braun-Unita l). The pH (pH meter 632, glass electrode EA 147; φ=5 mm, Metrohm) and, by titration with a freshly prepared 0.01 N NaOH solution to pH 7 (Dosimat 665 Metrohm), the secreted HCl were determined in the effluent in each case collected at an interval of 15 minutes.

The gastric secretion was stimulated by continuous infusion of 1 μg/kg (=1.65 ml/h) of i.v. pentagastrin (left femoral vein) about 30 min after the end of the operation (i.e. after determination of 2 preliminary fractions). The substances to be tested were administered intravenously in 1 ml/kg liquid volumes 60 min after the start of the pentagastrin continuous infusion.

The body temperature of the animals was kept at a constant 37.8–38° C. by infrared irradiation and heat pads (automatic, stepless control by means of a rectal temperature sensor).

What is claimed is:

1. A compound of the formula I

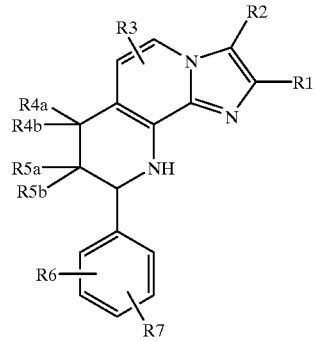

(I)

in which
R1 is 1–4C-alkyl,
R2 is 1–4C-alkyl or hydroxy-1–4C-alkyl,
R3 is hydrogen or halogen,
one of the substituents R4a and R4b is hydrogen and the other is hydrogen, hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which
one of the substituents R4a and R4b on the one hand and one of the substituents R5a and R5b on the other hand is in each case hydrogen, and the other substituents in each case together form a methylenedioxy radical (—O—CH₂—O—) or an ethylenedioxy radical (—O—CH₂—CH₂—O—),
where R4a, R4b, R5a and R5b are not simultaneously hydrogen,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl and
R7 is hydrogen, halogen, 1–4C-alkyl or 1–4C-alkoxy,
or a salt thereof.

2. The compound of formula I as claimed in claim 1, in which
R1 is 1–4C-alkyl,
R2 is 1–4C-alkyl or hydroxy-1–4C-alkyl,
R3 is hydrogen,
one of the substituents R4a and R4b is hydrogen and the other is hydrogen, hydroxyl or 1–4C-alkoxy, or in which R4a and R4b together are O (oxygen),
one of the substituents R5a and R5b is hydrogen and the other is hydrogen, hydroxyl or 1–4C-alkoxy, or in which R5a and R5b together are O (oxygen),
where R4a, R4b, R5a and R5b are not simultaneously hydrogen,
R6 is hydrogen, halogen or trifluoromethyl and
R7 is hydrogen or halogen
or a salt thereof.

3. The compound as claimed in claim 1, which has a formula I*

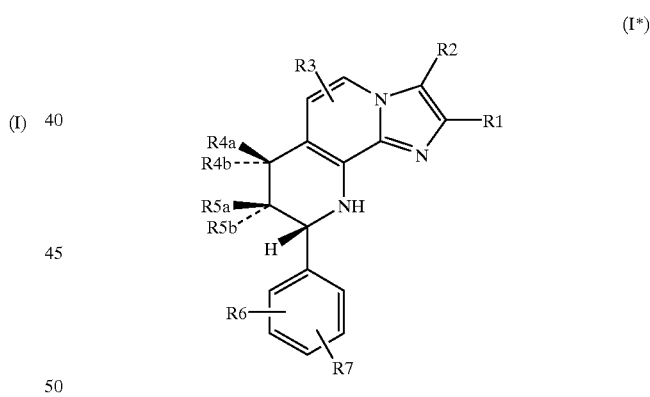

(I*)

in which
R1 is 1–4C-alkyl,
R2 is 1–4C-alkyl or hydroxy-1–4C-alkyl,
R3 is hydrogen,
one of the substituents R4a and R4b is hydrogen and the other is hydrogen, hydroxyl or 1–4C-alkoxy,
one of the substituents R5a and R5b is hydrogen and the other is hydrogen, hydroxyl or 1–4C-alkoxy,
where R4a, R4b, R5a and R5b are not simultaneously hydrogen,
R6 is hydrogen, halogen or trifluoromethyl and
R7 is hydrogen or halogen,
or a salt thereof.

4. A compound of a formula I* as claimed in claim 3, in which

R1 is 1–4C-akyl,
R2 is 1–4C-alkyl or hydroxymethyl,
R3 is hydrogen,
R4a is hydrogen,
R4b is hydroxyl or 1–4C-alkoxy,
R5a is hydrogen, hydroxyl or 1–4C-alkoxy,
R5b is hydrogen,
R6 is hydrogen, halogen or trifluoromethyl and
R7 is hydrogen or halogen,
or a salt thereof.

5. A compound of the a formula I* as claimed in claim 3, in which
R1 is 1–4C-alkyl,
R2 is 1–4C-alkyl,
R3 is hydrogen,
R4a is hydrogen,
R4b is hydroxyl,
R5a is hydroxyl,
R5b is hydrogen,
R6 is hydrogen, halogen or trifluoromethyl and
R7 is hydrogen or halogen,
or a salt thereof.

6. The compound selected from a group consisting of
7,8-dihydroxy-2,3-dimethyl-9-phenyl-7,8,9,10-tetrahydroimidazo[1,2-h][1,7]naphthyridine,
2,3-dimethyl-9-phenyl-7,8,9,10-tetrahydroimidazo[1,2-h][1,7]naphthyridin-7-one,
9-(2-chlorophenyl)-2,3-dimethyl-7,8,9,10-tetrahydroimidazo[1,2h][1,7]naphthyridin-7-one,
9-(2,6-dichlorophenyl)-2,3-dimethyl-7,8,9,10-tetrahydroimidazo[1,2-h][1,7]naphthyridin-7-one,
9-(2-trifluoromethylphenyl)-2,3-dimethyl-7,8,9,10-tetrahydroimidazo[1,2-h][1,7]naphthyridin-7-one,
7-hydroxy-2,3-dimethyl-9-phenyl-7,8,9,10-tetrahydroimidazo[1,2-h][1,7]naphthyridine,
9-(2-chlorophenyl)-7-hydroxy-2,3-dimethyl-7,8,9,10-tetrahydroimidazo[1,2-h][1,7]naphthyridine,
9-(2,6-dichlorophenyl)-7-hydroxy-2,3-dimethyl-7,8,9,10-tetrahydroimidazo[1,2-h][1,7]naphthyridine,
9-(2-trifluoromethylphenyl)-7-hydroxy-2,3-dimethyl-7,8,9,10-tetrahydroimidazo[1,2-h][1,7]naphthyridine,
8-hydroxy-2,3-dimethyl-9-phenyl-7,8,9,10-tetrahydroimidazo[1,2-h][1,7]naphthyridin-7-one,
(7S,8R,9R)-2,3-Dimethyl-7,8-dihydroxy-9-phenyl-7,8,9,10-tetrahydroimidazo[1,2-h][1,7]naphthyridine,
(8R,9R)-3-Formyl-8-hydroxy-2-methyl-7-oxo-9-phenyl-7,8,9,10-tetrahydroimidazo[1,2-h][1,7]naphthyridine,
(7R,8R,9R)-3-Hydroxymethyl-7,8-dihydroxy-2-methyl-9-phenyl-7,8,9,10-tetrahydroimidazo[1,2-h][1,7]naphthyridine and
(7S,8R,9R)-7,8-Isopropylidenedioxy-2,3-dimethyl-9-phenyl-7,8,9,10-tetrahydroimidazo[1,2-h][1,7]naphthyridine,
or a salt thereof.

7. A compound as claimed in claim 6 with 9R-configuration, or a salt thereof.

8. The compound as claimed in claim 1 having the chemical name (7R,8R,9R)-7,8-dihydroxy-2,3-dimethyl-9-phenyl-7,8,9,10-tetrahydroimidazo[1,2-h][1,7]naphthyridine, or a salt thereof.

9. A medicament composition comprising a compound as claimed in claim 1 and/or a pharmacologically tolerable salt thereof together with a customary pharmaceutical auxiliary and/or excipient.

10. A method of preventing or treating an amenable gastrointestinal disease by administering an effective amount of active ingredient to a warm-blooded animal in need of such therapy, wherein the active ingredient is a compound of formula I as claimed in claim 1, or a pharmacologically tolerable salt thereof.

11. A method of compounding a medicament composition by combining an active ingredient for preventing or treating a gastrointestinal disease with a customary pharmaceutical auxiliary and/or excipient, wherein the active ingredient is a compound of formula I as claimed in claim 1 or a pharmacologically tolerable salt thereof.

12. A medicament composition comprising a compound as claimed in claim 6 and/or a pharmacologically tolerable salt thereof together with a customary pharmaceutical auxiliary and/or excipient.

13. A method of preventing or treating an amenable gastrointestinal disease by administering an effective amount of active ingredient to a warm-blooded animal in need of such therapy, wherein the active ingredient is a compound as claimed in claim 6, or a pharmacologically tolerable salt thereof.

14. A method of compounding a medicament composition by combining an active ingredient for preventing or treating a gastrointestinal disease with a customary pharmaceutical auxiliary and/or excipient, wherein the active ingredient is a compound of claim 6 or a pharmacologically tolerable salt thereof.

* * * * *